United States Patent

Sarkisian et al.

Patent Number: 5,425,777
Date of Patent: Jun. 20, 1995

[54] ARTIFICIAL FINGER JOINT

[76] Inventors: James S. Sarkisian, 2276 Juan St., San Diego, Calif. 92103; Clarence F. Batchelder, 17087 Skyline Truck Trail, Jamul, Calif. 91935-3632

[21] Appl. No.: 218,708

[22] Filed: Mar. 25, 1994

Related U.S. Application Data

[63] Continuation of Ser. No. 995,773, Dec. 23, 1992, abandoned.

[51] Int. Cl.⁶ .............................................. A61F 2/42
[52] U.S. Cl. ........................................ 623/21; 623/18; 623/20; 606/76
[58] Field of Search ................ 606/76; 623/18, 19, 623/20, 21, 22

[56] References Cited

U.S. PATENT DOCUMENTS

| | | | |
|---|---|---|---|
| 4,229,841 | 10/1980 | Youm et al. | 3/1.91 |
| 4,242,759 | 1/1981 | White | 623/21 |
| 4,349,922 | 9/1982 | Agee | 3/1.91 |
| 4,352,212 | 10/1982 | Greene et al. | 3/1.91 |
| 4,790,851 | 12/1988 | Suire et al. | 623/23 |
| 4,944,758 | 7/1990 | Bekki et al. | 623/21 |
| 4,959,071 | 9/1990 | Brown et al. | 623/20 |
| 5,007,932 | 4/1991 | Bekki et al. | 623/21 |
| 5,047,059 | 9/1991 | Saffar | 623/21 |
| 5,147,386 | 9/1992 | Carignan et al. | 523/21 |

FOREIGN PATENT DOCUMENTS 0029787  6/1981  European Pat. Off. .............. 606/76

*Primary Examiner*—Paul Prebilic
*Attorney, Agent, or Firm*—Nydegger & Associates

[57] ABSTRACT

A metallic implantable finger joint has a biocompatible protective coating and includes both a base member and a protraction member. The base member is formed with a recess and has a protrusion projecting from inside the recess. The protraction member has a hemispherical surface which is slidingly engageable with the recess of the base member. Additionally, the protraction member is formed with a groove which engagingly receives the protrusion from the base member. This engagement is such that when the base member is juxtaposed with the protraction member, the interaction between the protrusion and the groove allows for relative movement between the members in flexion-extension, lateral rotation and pure rotation. The finger joint can also include implant barbs which are selectively engageable with the base member and the protraction member.

16 Claims, 2 Drawing Sheets

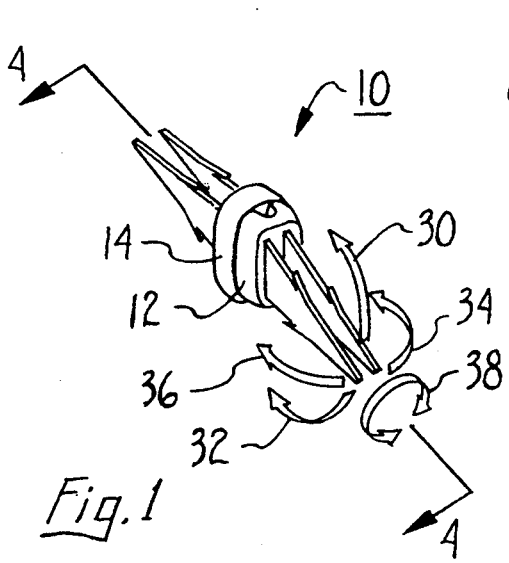
Fig. 1
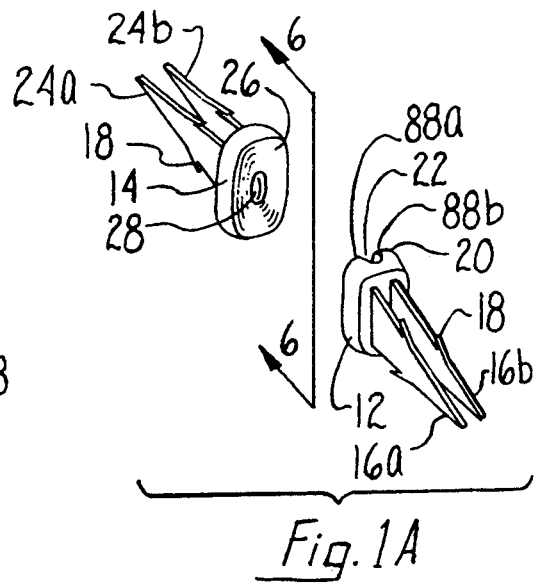
Fig. 1A
Fig. 2A
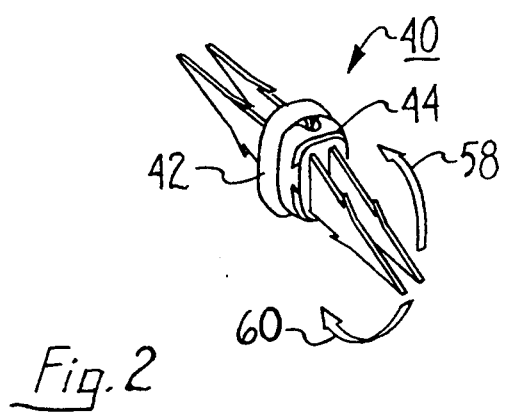
Fig. 2
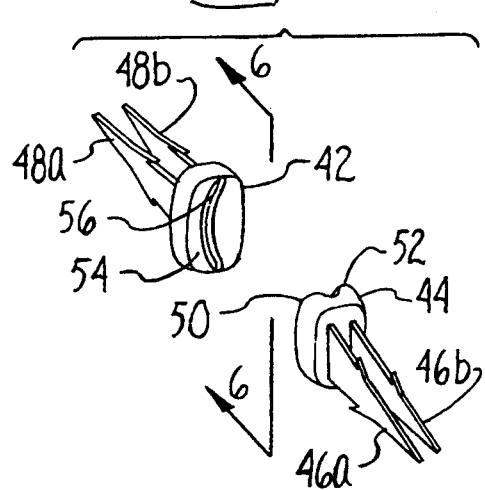
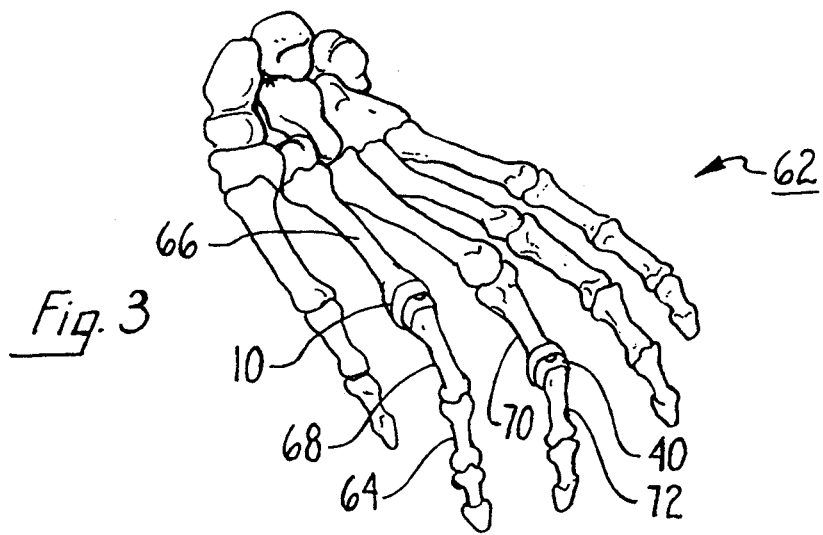
Fig. 3

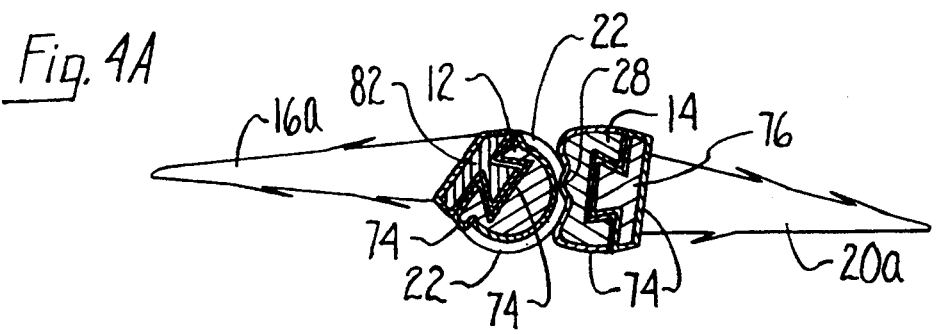
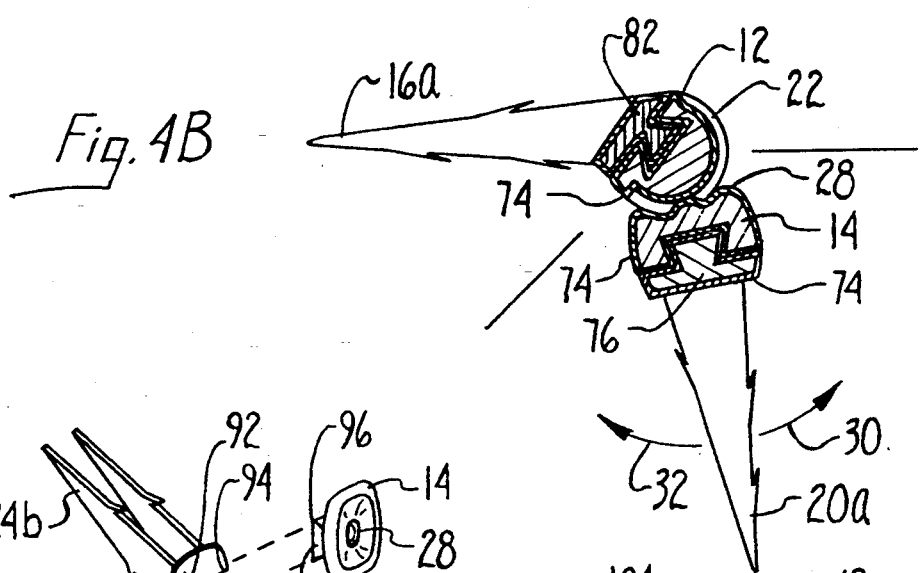
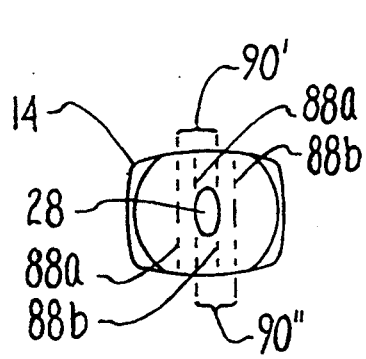
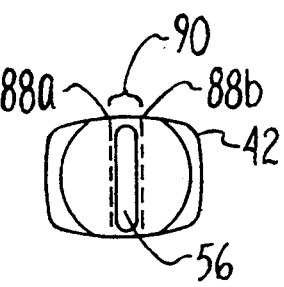

ARTIFICIAL FINGER JOINT

This is a continuation of U.S. application Ser. No. 07/995,773, filed on Dec. 23, 1992 and now abandoned.

TECHNICAL FIELD

The present invention pertains generally to implantable joints. More particularly, the present invention pertains to implantable finger joints which are made of metal and which are plated with a protective coating of a biocompatible material. The present invention is particularly, but not exclusively, useful as a finger joint which allows movement of the finger in flexion-extension, lateral rotation and pure rotation.

BACKGROUND OF THE INVENTION

It is known there are many materials that can not be implanted into the human body. Moreover, with any implant, there is always concern for the possibility of a toxic reaction and a complete rejection of the implant by the body. On the other hand, circumstances do occur when it may be desirable or necessary to implant foreign matter into the body. To help address this need, there has been much research and many development efforts undertaken to determine what implant materials are biocompatible with the human body. Although there have been some successes in solving this problem, much still remains to be done.

In addition to resolving the basic question concerning whether a proposed implant material is biocompatible with the human body, it must also be determined whether the implant material is functional for its intended purpose. To make this functional determination, a major consideration involves whether the implant is to be static or have dynamic characteristics. One set of problems are encountered if the implant structure is to remain static. Quite a different set of problems can be encountered, however, when dynamics are involved and the implant includes a bearing surface which must abut and slide against the bearing surface of another implant. An artificial finger joint is exemplary of such a structure.

In the past, various materials have been suggested for use in the manufacture of body joints. For example, polyethylene and other types of plastic have been tried for such structures. Unfortunately, plastic materials have had only minimal success. Stronger materials, such as metals, have been found to be preferable.

For purposes of manufacturing implants, metals introduce inherent problems which have heretofore obscured their utility. For example, metals tend to corrode in the body. An adverse effect from this fact is that the resultant corrosive products encourage the development of a fibrous membrane of connective tissue which surrounds the implants and is rejected by the body. Also, metals create toxic reactions in the body. It happens, however, some benefit may derive from such toxic reactions. Specifically, it is known that certain metals cause toxic reactions which inhibit the growth of the fibrous membrane. Titanium is such a metal and, despite its potential dielectric, titanium appears to be somewhat biocompatible.

The present invention recognizes that a titanium element, which is properly plated with a protective covering, can be implanted into a human body with tolerable consequences. Specifically, the present invention recognizes that by properly plating or coating the articular surfaces of a titanium implant, any toxic dielectric substance can be hidden from the body's immune discovery system.

As implied above, in addition to the biocompatibility concerns, an implant must also be capable of performing its intended function. Among the various body joints, artificial finger joints present their own unique circumstances. This is so, in part, due to the degrees of freedom which are necessary. For instance, a metacarpophalangeal artificial joint should provide freedom of movement at the joint for the movements of flexion-extension, lateral rotation, and axial rotation. Being more restrictive, an interphalangeal artificial joint need provide for movement in only flexion-extension. In either case, relative movement at the interface between the two bearing surfaces of the artificial joint is necessary. To satisfy these requirements, there must be sufficient durability in the materials for long term usage. Additionally, the artificial joint must be designed with sufficient structural constraints to maintain the relative movement of the joints parts within desired parameters. Also, as stated above, there must be biocompatability between the materials used to manufacture the components of the artificial joint and the human body.

In light of the above it is an object of the present invention to provide an artificial finger joint with components which can be reliably fixed to the skeletal structure of a patient. Another object of the present invention is to provide an artificial finger joint which includes bearing surfaces at the interface between components of the finger joint that are durable and that have useful longevity. Still another object of the present invention is to provide an artificial finger joint which is modular to allow for proper sizing and finger balance. Yet another object of the present invention is to provide an artificial finger joint which is of an all-metal construction. Another object of the present invention is to provide an artificial finger joint which is relatively easy to manufacture and comparatively cost effective.

SUMMARY OF THE INVENTION

An artificial finger joint in accordance with the present invention includes a base member which is juxtaposed with a protraction member. As intended for the present invention, these members slide relative to each other at their interface to accomplish the desired articulation for the finger joint.

The base member of the artificial finger joint is formed with a concave hemispherical shaped articular recess, and the protraction member is formed with a convex hemispherical shaped articular surface which mates with the recess. The degree and extent of relative movement of the members is determined by the interaction between a groove which is formed into the convex surface of the protraction member, and a protrusion which projects from inside the recess of the base member. For the present invention, the protrusion on the base member is received in the groove on the protraction member when the members are juxtaposed with one another.

In one embodiment of the present invention, the base and protraction members are juxtaposed to act as an interphalangeal joint. For the interphalangeal joint, the protrusion from the base member is dimensioned to fit snugly within the groove of the protraction member. This interaction allows only linear movement of the protrusion along the length of the groove. Consequently, relative movement between the members is limited to a flexion-extension motion for the finger joint.

In another embodiment for the finger joint of the present invention, the base and protraction members are juxtaposed to act as a metacarpophalangeal joint. For the metacarpophalangeal joint, the protrusion from the base member is dimensionally smaller than the groove in the protraction member to allow for both linear and rotational movement of the protrusion within the groove. Consequently, while the protrusion remains in the groove, relative movement between the base member and the protraction member is possible in flexion-extension, lateral rotation and axial rotation.

The artificial finger joints of the present invention also include barbed arms which are implantable into the skeletal structures that are to be connected by the artificial joint. In accordance with the present invention, the barbed arms may either be individually integral with the base member and the protraction member, or they may be of modular construction and selectively engageable with these members.

For the present invention, all components are preferably made of a titanium alloy which is electroplated or coated with a biocompatible protective coating. Further, it is preferable for the protective coating to be an inert heavy metal or selected from a group consisting of nitride, carbide, ceramic, oxide, carbonate and diamond.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 1 is a perspective view of a metacarpophalangeal artificial joint of the present invention;

FIG. 1A is an exploded perspective view of the joint shown in FIG. 1;

FIG. 2 is a perspective view of an interphalangeal artificial joint of the present invention;

FIG. 2A is an exploded perspective view of the joint shown in FIG. 2;

FIG. 3 is a perspective view of the skeletal structure of the fingers of a hand with implanted artificial joints in accordance with the present invention;

FIG. 4A is a cross-sectional view of the metacarpophalangeal artificial joint of the present invention as seen along the line 4—4 in FIG. 1, with the artificial joint in full extension;

FIG. 4B is a view of the joint shown in FIG. 4A with the joint in flexion;

FIG. 5 is an exploded perspective view of the artificial joint of the present invention showing its modular construction;

FIGS. 6A and 6B are plan views of the base member of the metacarpophalangeal joint as seen along the line 6—6 in FIG. 1A;

FIG. 6C is a plan view of the base member of the interphalangeal joint as seen along the line 6—6 in FIG. 2A; and FIG. 7 is an elevational plan view of an embodiment of the protraction member with portions shown in phantom.

DESCRIPTION OF PREFERRED EMBODIMENTS

Referring initially to FIG. 1, an artificial metacarpophalangeal (MCP) joint in accordance with the present invention is shown and generally designated 10. As shown, the MCP joint 10 includes a protraction member 12 which abuts and is slidingly engaged with a base member 14. Importantly, the surfaces of protraction member 12 and base member 14 are appropriately dimensioned to establish a separation of approximately fifteen ten thousandths of an inch (0.0015 in.) therebetween. This is done in order to allow synovial fluid to flow between the members 12,14 to provide lubrication in the joint 10.

As perhaps best seen in FIG. 1A, a pair of substantially parallel arms 16a, and 16b, extend from protraction member 12. The arms 16a,b are formed with barbs 18 which assist in the fixation of protraction member 12 to the skeletal structure of the person receiving the implant of artificial MCP joint 10. FIG. 1A also shows that protraction member 12 is formed with a rounded, substantially hemispherical, convex articular engaging surface 20, and that the articular surface 20 is formed with a circumferential groove 22. To be engageable with protraction member 12, the base member 14 of MCP joint 10 is formed with a recessed, substantially hemispherical, concave articular receiving surface 26 which is dimensioned to slidingly receive the engaging surface 20 of protraction member 12. Additionally, a mounded protrusion 28 extends outwardly from the recessed articular receiving surface 26 of base member 20 for insertion into the groove 22 when base member 14 is engaged with protraction member 12.

Returning to FIG. 1, it is to be appreciated that MCP joint 10 for the present invention is intended to allow movement of the finger distally from joint 10 in extension-flexion as indicated by the arrows 30/32. Specifically, extension of the finger is accomplished by movement in the direction of arrow 30, while flexion is accomplished by movement in the direction of arrow 32. Simultaneously, MCP joint 10 is intended to allow lateral rotation at the joint 10 in the directions indicated by the arrow 34/36. Also, and again simultaneously with the other possible movements, MCP joint 10 is intended to allow axial rotation of the finger distal to joint 10 in the directions indicated by the arrow 38. All of the above described movements result from the interaction between the protrusion 28 of base member 14 and the groove 22 of protraction member 12 as the members 12 and 14 slidingly abut each other. The exact manner for this interaction is to be subsequently discussed.

FIG. 2 shows an artificial interphalangeal (IP) joint in accordance with the present invention which is generally designated 40. IP joint 40 is shown to include a base member 42 and a protraction member 44. With a structure similar to that previously disclosed for MCP joint 10, IP joint 40 also has barbed arms 46a,b and barbed arms 48a,b which extend respectively from protraction member 44 and from base member 42. Also, similar to the protraction member 12 of MCP joint 10, protraction member 44 of IP joint 40 is formed with a rounded, substantially hemispherical, convex articular engaging surface 50 having a circumferential groove 52. Base member 42 of IP joint 40, however, differs somewhat from base member 14 of MCP joint 10. Although base member 42, like base member 14, is formed with a recessed, substantially hemispherical, concave articular receiving surface 54, unlike base member 14, the base member 42 of IP joint 40 has a ridge-like protrusion 56 which extends from its articular receiving surface 54 for insertion into groove 52 of protraction member 44. More specifically, the protrusion 56 is dimensioned for a snug fit into the groove 52 so that protrusion 56 is confined to only linear movement along the groove 52. The consequences of this structural interaction is best shown in FIG. 2.

From FIG. 2 it is to be appreciated that the relative movement between base member 42 and protraction member 44 is, as indicated by the arrows 58/60, is limited to only in flexion-extension. This is so because of the confined movement of protrusion 56 along the length of groove 52. More specifically, due to the snug fit between protrusion 56 and groove 52, protrusion 56 is unable to rotate within the groove 52.

In FIG. 3 the skeletal structure for part of a patient's hand is shown and generally designated 62. There it will be seen that an MCP joint 10 is inserted into a finger 64 between the metacarpal bone 66 and the proximal phalanx 68. Also, it will be seen that an IP joint 40 is inserted into another finger in the skeletal structure 62 between the proximal and middle phalanges 70/72. In each instance the joint 10 or 40 is enclosed in the skeletal structure 62 by inserting their respective barbed arms into the adjoining bone structure. The particular procedure for accomplishing this operation is left to the discretion of the surgeon and is not necessary for an understanding of the present invention.

FIGS. 4A and 4B illustrate an important aspect of the present invention which is applicable to both artificial MCP joint 10 and artificial IP joint 40. This aspect is a protective coating 74 which is deposited or plated onto base members 14,42 and onto protraction members 12,44. More specifically, it is necessary for the protective coating 74 to cover the respective articular surfaces of the members 12,14,42,44. Protective coating 74 can be deposited onto the articular surfaces of these members in any manner well known in the pertinent art, such as by electroplating. For purposes of the present invention, base members 14,42 and protraction members 12,44 are preferably made of a titanium metal alloy, although a ceramic, a carbide or an aluminum structure would also suffice. Further, the protective coating 74 is preferably a titanium nitride. Alternatively, however, the protective coating 74 can be selected from a group which consists of nitride, carbide, carbonate, ceramic, oxide and diamond. The preferred thickness for protective coating 74 is in the approximate range from three ten thousandths of an inch to ten ten thousandths of an inch (0.0003–0.0010 in.).

FIG. 5 shows the modular feature of the present invention as incorporated into the MCP joint 10. Though MCP joint 10 is specifically considered here, it is to be understood that this modular feature also applies equally to the IP joint 40. As shown in FIG. 5, base member 14 is interlockingly engageable with an attachment 76. More specifically, arms 24a,b extend from the attachment 76 and the attachment 76 is formed with an angled slot 78 which is dimensioned to receive the angled projection 80 that is formed as part of base member 14. Similarly, protraction member 12 is interlockingly engageable with an attachment 82. Also similarly, arms 16a,b extend from the attachment 82 and the attachment 82 is formed with an angled slot 84 which is dimensioned to receive the angled projection 86 that is formed as part of the protraction member 12.

For the preferred embodiment of the present invention, the interlockability of base member 14 with attachment 76, and the interlockability of protraction member 12 with attachment 82, is best seen in FIG. 5. There it is shown that the angled slot 78 of attachment 76 is actually tapered so that the width of the angled slot 78 is less or narrower at its end 92 than at its end 94. The angled projection 80 of base member 14 is compatibly dimensioned to receive the angled slot 78 of attachment 76. Accordingly, the end 96 of angled projection 80 is substantially the same size as the end 92 of angled slot 78. In a similar manner the angled projection 86 is tapered and compatibly dimensioned to be received into the angled slot 84 of attachment 82. Specifically, end 98 of angled projection 86 is wider than the end 100 of the projection 86, and the end 100 is substantially the same size as the width of angled slot 84 at its end 102. It will be appreciated by the skilled artisan that with the tapers oriented as shown, the protraction member 12 and base member 14 will resist each other whenever there is relative lateral motion between them. With this modularity, the articular surfaces of both base members 14,42 and protraction members 12,44, as well as the members themselves, can be sized and dimensioned as desired to account for bone resection and ligament balancing.

Turning for the moment to FIG. 7, some of the more subtle structural characteristics of the present invention will be appreciated. Although protraction member 12 is shown, it is only exemplary and these subtleties apply equally to the base member 14 and to the modular embodiments of the present invention. First, it will be seen that the base member 12 is formed with holes 104 and 110, and that these holes lead into channels 108 and 112 (shown in phantom) which exit from the base member 12 at other holes (not shown). Frequently, as is well known in the pertinent art, an artificial joint 10,40 requires ligament attachment. Accordingly, the purpose of the holes 104,110 and their channels 108,112 is to allow for the replacement of diseased or deficient ligaments with suitable sutures.

FIG. 7 also shows that the barbs 18 on arms 16a,b are outwardly angled, and away from the opposing arm 16, through an angle 114. For purposes of the present invention the angle 114 may be in the range of from fifteen to fifty degrees. Further, FIG. 7 shows that the arms 16a,b are towed-in relative to each other. More specifically, the distance 116 between the exposed ends of the arms 16a,b is less than the distance 118 between the ends of the arms 16a,b which are attached to the protraction member 12. The outwardly angled barbs 18 provide additional anchorage for the members by helping to prevent the thin edge of arms 16 from cutting into the bone. Together, the outwardly angled barbs 18 and the tow-in feature of the arms 16a,b help inhibit an abnormal erosion of the bony canal into which the arms 16 of the joint 10,40 anchored. This improves both the anchorage of the joint 10,40 and its longevity.

As stated above, articulation of MCP joint 10 involves flexion-extension, lateral rotation, and axial rotation. These various movements are best appreciated by cross referencing between several Figures. To begin, consider the flexion-extension motion of MCP joint 10 and refer to FIGS. 1, 4A and 4B. As indicated above, and shown in FIG. 1, extension is accomplished by movement in the direction of arrow 30 and flexion is accomplished by movement in the direction of arrow 32. FIGS. 4A and 4B show that during a flexion-extension movement of joint 10, the mounded protrusion 28 of base member 14 moves linearly along the groove 22 of protraction member 12. Also, as with all operational functions of the joint 10, base member 14 is juxtaposed and slidingly engaged with protraction member 12. For purposes of the present invention, groove 22 should be of sufficient length to allow for flexion-extension movement in the directions of arrows 30/32 through a range of approximately one hundred and fifty degrees (150°).

Lateral rotation of MCP joint 10 is best appreciated by cross referencing FIG. 1A and FIG. 6A. In FIG. 1A the opposing edges of groove 22 are numerically identified as 88a and 88b. In FIG. 6A, the edges 88a and 88b are shown in phantom as they would be located on the recessed articular receiving surface 26 of base member 14. As shown in FIG. 6A the edges 88a and 88b are distanced from each other by a spacing 90. Further, for MCP joint 10, spacing 90 is sufficiently larger than the dimensions of protrusion 28 to permit a selective movement of protraction member 12 between spacing 90' and spacing 90". This results in a lateral rotation of protraction member 12 relative to base member 14 in the directions of arrows 34/36 through a range of approximately fifty degrees (50°).

Axial rotation of MCP joint 10 is best appreciated by cross referencing FIG. 1A with FIG. 6B. In this case, the size of protrusion 28 is seen to be such that protraction member 12 is able to axially rotate relative to base member 14 in the direction of arrow 38. Specifically, as seen in FIG. 6B, spacing 90 between the edges 88a,b is sufficiently larger than the dimensions of protrusion 28 to permit a selective movement of protraction member 12 between spacing 90''' and 90''''. This results in an axial rotation of protraction member 12 relative to base member 14 in the direction of arrow 38. For purposes of the present invention, axial rotation of the protraction member 12 is preferably in the range of approximately fifty degrees (50°).

It is to be appreciated that flexion-extension, lateral rotation, and axial rotation of protraction member 12 relative to base member 14 can be accomplished either independently or simultaneously in concert with any of the other movements. IP joint 40, on the other hand, is more constrained.

Cross referencing FIG. 2B with FIG. 6C shows that for IP joint 40, the ridge-like protrusion 56 on base member 42 fits snugly within the groove 52 of protraction member 44. The result is that there can be no lateral rotation or axial rotation of protraction member 44 relative to base member 42. Instead, only flexion-extension movement is possible. In all other respects, to include incorporation of a protective coating 74 and the modularity feature disclosed above, IP joint 40 is substantially similar to MCP joint 40.

While the particular artificial joints as herein shown and disclosed in detail are fully capable of obtaining the objects and providing the advantages herein before stated, it is to be understood that they are merely illustrative of the presently preferred embodiments of the invention and that no limitations are intended to the details of the construction or design herein shown other than as defined in the appended claims.

We claim:

1. An artificial finger joint which comprises:
   a first member having a rounded articular surface formed with a groove;
   a second member juxtaposable with said first member and having a recessed articular surface for slidingly receiving said rounded surface of said first member therein; and
   an elongated protrusion projecting from said recessed surface of said second member for insertion into said groove on said first member said protrusion being dimensioned relatively smaller than said groove to establish a sliding movement for said rounded articular surface of said first member over said recessed articular surface of said second member to permit limited lateral rotation and limited axial rotation of said joint as said first member is juxtaposed with said second member, said groove and said protrusion, when fully engaged, are dimensioned to limit lateral rotation movement through a range of approximately fifty degrees and said axial rotation movement through a range of approximately fifty degrees.

2. An artificial finger joint as recited in claim 1 wherein said first member and said second member are made of a titanium alloy plated with a protective coating.

3. An artificial finger joint as recited in claim 2 wherein said protective coating is titanium nitride.

4. An artificial finger joint as recited in claim 1 wherein said flexion-extension movement is accomplished through a range of approximately one hundred and fifty degrees (150°).

5. An artificial finger joint as recited in claim 1 wherein said joint is implantable in the hand of a patient and said joint further comprises means for fixedly attaching said first member to the skeletal structure of said hand and means for fixedly attaching said second member to the skeletal structure of said hand.

6. An artificial finger joint as recited in claim 5 wherein said first member attaching means and said second member attaching means each has a barb outwardly angled from said attaching means for anchoring said attaching means to said skeletal structure.

7. An artificial finger joint as recited in claim 5 wherein said first member is selectively attachable to said first member attaching means and said second member is selectively attachable to said second member attaching means.

8. An artificial finger joint as recited in claim 2 wherein said protective coating is selected from the group consisting of carbonate, ceramic, and diamond.

9. An artificial finger joint which comprises:
   an implantable base formed with a recessed receiving articular surface having an elongated protrusion projecting therefrom, said base being plated with a biocompatible protective coating; and
   an implantable member formed with an engaging articular surface formed with a groove, said member being plated with a biocompatible protective coating and juxtaposable with said base to slide said engaging surface over said receiving surface with said protrusion inserted in said groove, said protrusion being dimensioned relatively smaller than said groove to establish a sliding movement between said receiving articular surface and said engaging articular surface to accomplish a flexion-extension movement, a limited lateral rotation, and a limited axial rotation for said joint when said base is juxtaposed with said member, said groove and said protrusion, when fully engaged, are dimensioned to limit lateral rotation movement through a range of approximately fifty degrees and said axial rotation movement through a range of approximately fifty degrees.

10. An artificial finger joint as recited in claim 9 wherein said base and said member are made of a titanium alloy and said protective coating is selected from the group consisting of carbonate, ceramic, and diamond.

11. An artificial finger joint as recited in claim 10 wherein said protrusion from said base is dimension to fit snugly into said groove of said member to limit movement of said protraction relative to said base to a flexion-extension motion accomplished through a range of approximately one hundred and fifty degrees (150°).

12. An artificial finger joint as recited in claim 10 wherein said protrusion is dimensioned to permit a sliding movement of said member relative to said base to accomplish a flexion-extension movement through a range of approximately one hundred and fifty degrees (150°), a lateral rotational movement through a range of approximately fifty degrees (50°), and a pure rotational movement through a range of approximately fifty degrees (50°).

13. An artificial finger joint as recited in claim 9 wherein said joint is implantable in the hand of a patient and said joint further comprises means for fixedly attaching said base to the skeletal structure of said hand and means for fixedly attaching said member to the skeletal structure of said hand.

14. An artificial finger joint as recited in claim 13 wherein said base attaching means and said member attaching means each has a barb outwardly angled from said attaching means for anchoring said respective attaching means to said skeletal structure.

15. An artificial finger joint as recited in claim 13 wherein said base is selectively attachable to said base attaching means and said member is selectively attachable to said member attaching means.

16. An artificial finger joint as recited in claim 9 wherein said base and said member are made of titanium alloy and said protective coating is titanium nitride.

* * * * *